US005969096A

United States Patent [19]
Shon et al.

[11] Patent Number: 5,969,096
[45] Date of Patent: Oct. 19, 1999

[54] CONOTOXIN PEPTIDES

[75] Inventors: Ki-Joon Shon, Shaker Heights, Ohio; William R. Gray, Salt Lake City, Utah; John Dykert, Vista, Calif.; Doju Yoshikami, Salt Lake City, Utah; Maren Watkins, Salt Lake City, Utah; David R. Hillyard, Salt Lake City, Utah; Jean E. F. Rivier, La Jolla, Calif.; Baldomero M. Olivera, Salt Lake City, Utah

[73] Assignees: The Salk Institute for Biological Studies, La Jolla, Calif.; University of Utah Research Foundation, Salt Lake City, Utah

[21] Appl. No.: 09/105,715

[22] Filed: Jun. 26, 1998

[51] Int. Cl.$^6$ .................................................. A61K 38/00
[52] U.S. Cl. .............................. 530/325; 514/13
[58] Field of Search ................................ 530/325; 514/13

[56] References Cited

U.S. PATENT DOCUMENTS

| 5,432,155 | 7/1995 | Olivera et al. | 514/12 |
| 5,595,972 | 1/1997 | Olivera et al. | 514/13 |
| 5,633,347 | 5/1997 | Olivera et al. | 503/324 |
| 5,700,778 | 12/1997 | Olivera et al. | 514/12 |

OTHER PUBLICATIONS

Shon, et al., "A Non–competitive Inhibitor of the Nicotinic Acetlcholine Receptor fron *Conus purpurascens* Venom" Biochemistry 1997, 36, 9581.

Shon, et al., "Three–Dimensional Solution Structure of α–Conotoxin MII, an $\alpha_3\beta_2$ Neuronal Nicotinic Acetylcholine Receptor–Targeted Ligand", Reprinted from *Biochemistry*, vol. 36(50):15693–15700 (1997).

Advance ACS Abstract, Jul. 1, 1997, K. Shoen, et al., "Society for Neuroscience", 27th Annual Meeting, 1997.

Shon, et al., "A Noncompetitive Peptide Inhibitor of the Nicotinic Acetylcholine Receptor from *Conus purpurascens* Venom", *Biochemistry*, 36:9581–9587, 1997.

*Primary Examiner*—Cecilia J. Tsang
*Assistant Examiner*—Fabian A. Jameison
*Attorney, Agent, or Firm*—Fitch, Even, Tabin & Flannery

[57] ABSTRACT

Substantially pure conotoxin peptides are provided which inhibit synaptic transmissions at the neuromuscular junctions and which are useful both in vivo and in assays because they specifically target particular skeletal nAChRs to the exclusion of neuronal nAChRs. The peptides are of such length that they can be made by chemical synthesis, and the preferred peptides have formula: H-His-4Hyp-4Hyp-Cys-Cys-Leu-Tyr-Gly-Lys-Cys-Arg-Arg-Tyr-4Hyp-Gly-Cys-Ser-Ser-Ala-Ser-Cys-Cys-Gln-$Xaa_{24}$-$NH_2$ wherein $Xaa_{24}$ is Arg or Gly.

11 Claims, No Drawings

SEQUENCE LISTING

```
<160> NUMBER OF SEQ ID NOS: 1

<210> SEQ ID NO 1
<211> LENGTH: 24
<212> TYPE: PRT
<213> ORGANISM: Artificial Sequence
<220> FEATURE:
<223> OTHER INFORMATION: Description of Artificial Sequence: Conotoxin
      Peptide Analog
<220> FEATURE:
<221> NAME/KEY: VARIANT
<222> LOCATION: (2)
<223> OTHER INFORMATION: Pro or 4Hyp
<220> FEATURE:
<221> NAME/KEY: VARIANT
<222> LOCATION: (3)
<223> OTHER INFORMATION: Pro or 4Hyp
<220> FEATURE:
<221> NAME/KEY: VARIANT
<222> LOCATION: (14)
<223> OTHER INFORMATION: Pro or 4Hyp
<220> FEATURE:
<221> NAME/KEY: VARIANT
<222> LOCATION: (24)
<223> OTHER INFORMATION: Arg or Gly

<400> SEQUENCE: 1

His Xaa Xaa Cys Cys Leu Tyr Gly Lys Cys Arg Arg Tyr Xaa Gly Cys
 1               5                  10                  15

Ser Ser Ala Ser Cys Cys Gln Xaa
            20
```

CONOTOXIN PEPTIDES

This invention was made with Government support under Grant Nos. GM-48677, GM-22737 and AM-26741, awarded by the National Institutes of Health. The Government has certain rights in this invention.

This invention relates to relatively short peptides, e.g. about 24 residues in length, and more particularly to peptides which are naturally available in only minute amounts in the venom of cone snails and which include a plurality of cyclizing disulfide linkages.

BACKGROUND OF THE INVENTION

Mollusks of the genus Conus produce a highly toxic venom which enables them to carry out their unique predatory lifestyle. Prey are immobilized by the venom which is injected by means of a highly specialized venom apparatus, a disposable hollow tooth which functions both in the manner of a harpoon and a hypodermic needle.

Few interactions between organisms are more striking than those between a venomous animal and its envenomated victim. Venom may be used as a primary weapon to capture prey or as a defense mechanism. These venoms disrupt essential organ systems in the envenomated animal, and many of these venoms contain molecules directed to receptors and ion channels of neuromuscular systems.

The predatory cone snails (Conus) have developed a unique biological strategy. Their venom contains relatively small peptides that are targeted to various neuromuscular receptors and may be equivalent in their pharmacological diversity to the alkaloids of plants or secondary metabolites of microorganisms. Many of these peptides are among the smallest nucleic acid-encoded translation products having defined conformations, and as such they are somewhat unusual. Peptides in this size range normally equilibrate among many conformations, and proteins having a fixed conformation are generally much larger.

The cone snails that produce these toxic peptides, which are generally referred to as conotoxins or conotoxin peptides, are a large genus of venomous gastropods comprising approximately 500 species. All cone snail species are predators that inject venom to capture prey, and the spectrum of animals that the genus as a whole can envenomate is broad. A wide variety of hunting strategies are used; however, every Conus species uses fundamentally the same basic pattern of envenomation.

The major paralytic peptides in these fish-hunting cone venoms were the first to be identified and characterized. In *C. geographus* venom, three classes of disulfide-rich peptides were found: the α-conotoxins (which target and block the nicotinic acetylcholine receptors); the μ-conotoxins (which target and block the skeletal muscle Na$^+$channels); and the ω-conotoxins (which target and block the presynaptic neuronal Ca$^{2+}$ channels). However, there are multiple homologs in each toxin class; for example, at least five different ω-conotoxins are present in *C. geographus* venom alone. Considerable variation in sequence is evident, and when different ω-conotoxin sequences were first compared, only the cysteine residues that are involved in disulfide bonding and one glycine residue were found to be invariant. Another class of conotoxins found in *C. geographus* venom is that referred to as the conantokins which cause sleep in young mice and hyperactivity in older mice and are targeted to the NMDA receptor. Each cone venom appears to have its own distinctive group or signature of different conotoxin sequences.

Many of these peptides have now become fairly standard research tools in neuroscience. The μ-conotoxins, because of their ability to preferentially block muscle but not axonal Na$^+$ channels, are convenient tools for immobilizing skeletal muscle without affecting axonal or synaptic events. U.S. Pat. No. 5,432,155 discloses a group of bioactive conotoxin peptides which are extremely potent inhibitors of synaptic transmission at the neuromuscular junction and/or which are targeted to specific ion channels. Many of them appear to be members of the known class of μ-conotoxins.

Nicotinic acetylcholine receptors (nAChRs) are ligand-gated ion channels which are key components of nervous systems. The classical role for these receptors was defined at the neuromuscular junction: nicotinic receptors concentrated on the muscle end plate serve as the key macromolecules that detect release of a neurotransmitter from the presynaptic terminus of the motor axon. However, in addition to these skeletal muscle nicotinic receptors, many other molecular forms of nicotinic receptors exist; these are generally referred to as neuronal nAChRs.

The ω-conotoxins have become standard pharmacological reagents for investigating voltage-sensitive Ca$^{2+}$ channels and are used to block presynaptic termini and neurotransmitter release. The ω-conotoxin GVIA from *C. geographus* venom, which binds to neuronal voltage-sensitive Ca$^{2+}$ channels, is an example of such. The affinity ($K_d$) of ω-conotoxin GVIA for its high-affinity targets is sub-picomolar; it takes more than 7 hours for 50% of the peptide to dissociate. Thus the peptide can be used to block synaptic transmission virtually irreversibly because it inhibits presynaptic Ca$^{2+}$ channels. However, ω-conotoxin is highly tissue-specific. In contrast to the standard Ca$^{2+}$ channel-blocking drugs (e.g. the dihydropyridines, such as nifedipene and nitrendipine, which are widely used for angina and cardiac problems), which can bind Ca$^{2+}$ channels in smooth, skeletal, and cardiac muscle as well as neuronal tissue, ω-conotoxins generally bind only to a subset of neuronal Ca$^{2+}$ channels, primarily of the N subtype. The discrimination ratio for ω-conotoxin binding to voltage-sensitive Ca$^{2+}$ channels in neuronal versus nonneuronal tissue (e.g. skeletal or cardiac muscle) is greater than 10$^8$ in many cases.

The α-conotoxins have various clinical uses. One such use is their utility as clinical muscle relaxants because of their ability to achieve antagonistic blockage of the mammalian neuromuscular junction nAChRs. Another use for the α-conotoxins is in the diagnosis of myasthenia gravis. Some α-conotoxins have been found to bind preferentially to neuronal nicotinic receptors rather than to neuromuscular receptors.

Examples of such peptides are shown in U.S. Pat. Nos. 5,432,155; 5,595,972 and 5,633,347, the disclosures of which are incorporated herein by reference.

Additional conotoxin peptides having these general properties continue to be sought.

SUMMARY OF THE INVENTION

The present invention provides bioactive conotoxin peptides which are paralytic as a result of inhibiting the muscle nicotinic acetylcholine receptors (nAChRs) and may be used for known therapeutic and diagnostic purposes. They may also be useful as pesticides, targetable to specific insects or other pests.

These conotoxin peptides have the formula set forth hereinafter:

His-Xaa$_2$-Xaa$_3$-Cys-Cys-Leu-Tyr-Gly-Lys-Cys-Arg-Arg-Tyr-Xaa$_{14}$-Gly-Cys-Ser-Ser-Ala-Ser-Cys-Cys-Gln- $Xaa_{24}$ (SEQ ID NO:1) wherein $Xaa_2$, $Xaa_3$ and $Xaa_{14}$ are independently Pro or 4Hyp (4-hydroxyproline); $Xaa_{24}$ is either Arg or Gly and the C-terminus is amidated.

The invention provides conotoxin peptides having 6 Cys residues interconnected by 3 disulfide bonds which bind certain ion channels. Two residues near the N-terminus and one near the center of the peptide are preferably 4Hyp; however, peptides having Pro at one or more of these positions also exhibit similar biological activities. The residue at the C-terminus is either Arg or Gly, and the C-terminus is amidated. These conotoxin peptides cause immediate paralysis in fish and, when administered intracranially to laboratory mice, are lethal, causing audiogenic seizures.

These peptides, which are generally termed Ψ-conotoxins, have been isolated from the venom of the fish-hunting purple cone *Conus purpurascens*; they are sufficiently small to be chemically synthesized. General chemical syntheses for preparing the foregoing conotoxins are described hereinafter along with one specific chemical synthesis and indications of biological activities of the synthetic product. Various of these conotoxins can also be obtained by isolation and purification from specific conus species using the technique described in U.S. Pat. No. 4,447,356 (May 8, 1984), the disclosure of which is incorporated herein by reference.

These conotoxin peptides have paralytic effects and are considered to interfere with neuromuscular transmission. At the same time, the peptides appear to lack any demonstrable inhibition of transmission of certain major neuronal nAChR subtypes. They are considered useful to relax certain skeletal muscles during surgery.

The activity of each of these conotoxin peptides is freely reversible upon dilution or removal of the toxin from the affected skeletal muscle. Moreover, toxicity of the cyclic peptides is generally destroyed by agents which disrupt disulfide bonds in the cyclic conotoxins, suggesting that correct disulfide bonding appears essential for biological activity; however, correct folding and/or rearrangement of a conotoxin may occur in vivo so that in some cases the linear peptide may be administered for certain purposes. However, the synthetic linear peptides fold spontaneously when exposed to air-oxidation at cold room temperatures to create the correct disulfide bonds to confer biological activity, and such processing is accordingly preferred. The conotoxins exhibit activity on a wide range of vertebrate animals, including humans, and on insects, and many are useful to reversibly immobilize skeletal muscles in humans or other vertebrate species. These conotoxin peptides may be useful for rapid reversible immobilization of skeletal muscles in vertebrate species, including humans, thereby facilitating the setting of fractures and dislocations. These conotoxin peptides may also be useful in medical diagnosis.

DETAILED DESCRIPTION OF THE PREFERRED EMBODIMENTS

Although the conotoxins can be obtained by purification from the enumerated cone snails, because the amounts of conotoxins obtainable by milking individual snails are very small, the desired substantially pure conotoxins are best practically obtained in commercially valuable amounts by chemical synthesis. For example, the yield from a single cone snail may be about 10 micrograms or less of conotoxin. By substantially pure is meant that the peptide is present in the substantial absence of other biological molecules of the same type; it is preferably present in an amount at least about 85% by weight and more preferably at least about 95% of such biological molecules of the same type which are present, i.e. water, buffers and innocuous small molecules may be present. Chemical synthesis of such biologically active conotoxin peptides depends of course upon knowledge of the correct amino acid sequence, i.e. that which is set forth hereinbefore.

Six cysteine residues are present in these conotoxins, and biological activity is destroyed by agents which break disulfide bonds, such as sodium borohydride or β-mercaptoethanol. Such indicates that a specific folded configuration, induced by disulfide cross-links, is essential for bioactivity of these conotoxins. It has been found that air-oxidation of the linear peptides for prolonged periods under cold room temperatures results in the creation of a substantial amount of the bioactive, disulfide-linked molecules. Therefore, the preferable procedure for making these peptides is to oxidize the linear peptide and then fractionate the resulting product, using reverse-phase high performance liquid chromatography (HPLC) or the like, to separate peptides having different linked configurations. Thereafter, either by comparing these fractions with the elution of the native material or by using a simple assay, the particular fraction having the correct linkage for maximum biological potency is easily determined. It is also found that the linear peptide, or the oxidized product having more than one fraction, can sometimes be used for in vivo administration, because the cross-linking and/or rearrangement which occurs in vivo has been found to create the biologically potent conotoxin molecule; however, because of the dilution resulting from the presence of other fractions of less biopotency, a somewhat higher dosage may be required.

A particularly useful characteristic of these conotoxins is their high affinity for particular macromolecular receptors, accompanied by a narrow receptor-target specificity. A major problem in medicine results from side effects which drugs very often exhibit, some of which are caused by the drug binding not only to the particular receptor subtype that renders therapeutic value, but also to closely related, therapeutically irrelevant receptor subtypes which can often cause undesirable physiological effects. In contrast to most drugs, these conotoxins generally discriminate among closely related receptor subtypes.

The peptides are synthesized by a suitable method, such as by exclusively solid-phase techniques, by partial solid-phase techniques, by fragment condensation or by classical solution couplings.

In conventional solution phase peptide synthesis, the peptide chain can be prepared by a series of coupling reactions in which the constituent amino acids are added to the growing peptide chain in the desired sequence. The use of various N-protecting groups, various coupling reagents, e.g., dicyclohexylcarbodiimide or carbonyldiimidazole, various active esters, e.g., esters of N-hydroxyphthalimide or N-hydroxysuccinimide, and the various cleavage reagents, to carry out reaction in solution, with subsequent isolation and purification of intermediates, is well known classical peptide methodology. Classical solution synthesis is described in detail in the treatise "Methoden der Organischen Chemie (Houben-Weyl): Synthese von Peptiden", E. Wunsch (editor) (1974) Georg Thieme Verlag, Stuttgart, W. Ger. Techniques of exclusively solid-phase synthesis are set forth in the textbook "Solid-Phase Peptide Synthesis", Stewart & Young, Pierce Chemical Co., Rockford, Ill., 1984, and are exemplified by the disclosure of U.S. Pat. No. 4,105,603. The fragment condensation method of synthesis is exemplified in U.S. Pat. No. 3,972,859. Other available syntheses are exemplified by U.S. Pat. Nos. 3,842,067 and 3,862,925.

Common to such chemical syntheses is the protection of the labile side chain groups of the various amino acid moieties with suitable protecting groups which will prevent a chemical reaction from occurring at that site until the group is ultimately removed. Usually also common is the protection of an alpha-amino group on an amino acid or a fragment while that entity reacts at the carboxyl group, followed by the selective removal of the alpha-amino protecting group to allow subsequent reaction to take place at that location. Accordingly, it is common that, as a step in such a synthesis, an intermediate compound is produced which includes each of the amino acid residues located in its desired sequence in the peptide chain with appropriate side-chain protecting groups linked to various of the residues having labile side chains.

As far as the selection of a side chain amino protecting group is concerned, generally one is chosen which is not removed during deprotection of the α-amino groups during the synthesis. However, for some amino acids, e.g. His, protection is not generally necessary. In selecting a particular side chain protecting group to be used in the synthesis of the peptides, the following general rules are followed: (a) the protecting group preferably retains its protecting properties and is not split off under coupling conditions, (b) the protecting group should be stable under the reaction conditions selected for removing the α-amino protecting group at each step of the synthesis, and (c) the side chain protecting group must be removable, upon the completion of the synthesis containing the desired amino acid sequence, under reaction conditions that will not undesirably alter the peptide chain.

These peptides are preferably prepared using the Merrifield solid phase synthesis, although other equivalent chemical syntheses known in the art can also be used as previously mentioned. Such solid-phase synthesis is commenced from the C-terminus of the peptide by coupling a protected α-amino acid to a suitable resin. Such a starting material can be prepared by attaching an α-amino-protected amino acid by an ester linkage to a chloromethylated resin or a hydroxymethyl resin, or by an amide bond to a benzhydrylamine (BHA) resin or paramethylbenzhydrylamine (MBHA) resin. The preparation of the hydroxymethyl resin is described by Bodansky et al., *Chem. Ind.* (London) 38, 1597–98 (1966). Chloromethylated resins are commercially available from Bio Rad Laboratories, Richmond, Calif. and from Lab. Systems, Inc. The preparation of such a resin is described by Stewart et al., "Solid Phase Peptide Synthesis", supra. BHA and MBHA resin supports are commercially available and are generally used when the desired polypeptide being synthesized has an unsubstituted amide at the C-terminus. Thus, solid resin supports may be any of those known in the art, such as one having the formulae: —O—CH$_2$-resin support, —NH BHA resin support or —NH—MBHA resin support. When the unsubstituted amide is desired, use of a BHA or MBHA resin is preferred, because cleavage directly gives the amide. In case the N-methyl amide is desired, it can be generated from an N-methyl BHA resin.

The C-terminal amino acid, protected by Boc and by a side-chain protecting group, if appropriate, can be first coupled to a chloromethylated resin according to the procedure set forth in *Chemistry Letters*, K. Horiki et al. 165–168 (1978), using KF in DMF at about 60° C. for 24 hours with stirring, when a peptide having free acid at the C-terminus is to be synthesized. Following the coupling of the BOC-protected amino acid to the resin support, the α-amino protecting group is removed, as by using trifluoroacetic acid(TFA) in methylene chloride or TFA alone. The deprotection is carried out at a temperature between about 0° C. and room temperature. Other standard cleaving reagents, such as HCl in dioxane, and conditions for removal of specific α-amino protecting groups may be used as described in Schroder & Lubke, "The Peptides", 1 pp 72–75, Academic Press (1965).

After removal of the α-amino protecting group, the remaining α-amino- and side chain-protected amino acids are coupled step-wise in the desired order to obtain the intermediate compound defined hereinbefore, or as an alternative to adding each amino acid separately in the synthesis, some of them may be coupled to one another prior to addition to the solid phase reactor. The selection of an appropriate coupling or activating reagent is within the skill of the art as such reagents for the solid phase synthesis of the peptides are well known in the peptide art. Particularly suitable coupling reagents are N,N'-dicyclohexylcarbodiimide (DCC), N,N'-diisopropylcarbodiimide and N-ethyl-N'-(3-dimethylaminopropyl)carbodiimide. Other activating reagents and their use in peptide coupling are described by Schroder & Lubke supra, in Chapter III and by Kapoor, *J. Phar. Sci.*, 59, pp 1–27 (1970).

Each protected amino acid or amino acid sequence is introduced into a solid phase reactor in about a twofold or more excess, and the coupling may be carried out in a medium of dimethylformamide(DMF): CH$_2$Cl$_2$ (1:1) or in DMF or CH$_2$Cl$_2$ alone. In cases where incomplete coupling occurs, the coupling procedure is repeated before removal of the α-amino protecting group prior to the coupling of the next amino acid. The success of the coupling reaction at each stage of the synthesis, if performed manually, is preferably monitored by the ninhydrin reaction, as described by E. Kaiser et al., *Anal. Biochem.* 34, 595 (1970). The coupling reactions can be performed automatically, as on a Beckman 990 automatic synthesizer, using a program such as that reported in Rivier et al. *Biopolymers*, 1978, 17, pp 1927–1938.

After the desired amino acid sequence has been completed, the intermediate peptide can be removed from the resin support by treatment with a reagent, such as liquid hydrogen fluoride (HF), which not only cleaves the peptide from the resin but also cleaves all remaining side chain protecting groups and also the α-amino protecting group at the N-terminus if it was not previously removed to obtain the peptide in the form of the free acid. When using hydrogen fluoride for cleaving, one or more scavengers, such as anisole, cresol, dimethyl sulfide, and methylethyl sulfide are commonly included in the reaction vessel.

Cyclization of the linear peptide is preferably effected, as opposed to cyclizing the peptide while a part of the peptidoresin, to create bonds between Cys residues. To effect such disulfide cyclizing linkages, the fully protected peptide can be cleaved from a hydroxymethylated resin or a chloromethylated resin support by ammonolysis, as is well known in the art, to yield the fully protected amide intermediate, which is thereafter suitably cyclized and deprotected. Alternatively, deprotection as well as cleavage of the peptide from a benzhydrylamine (BHA) resin or a methylbenzhydrylamine (MBHA) resin, can take place at 0° C. with hydrofluoric acid (HF), followed by air-oxidation under high dilution conditions.

In order to illustrate specific preferred embodiments of the invention in greater detail, the following exemplary work is provided.

EXAMPLE 1

Conotoxin Peptide No. 1, having the chemical formula (SEQ ID NO:1):

H-His-4Hyp-4Hyp-Cys-Cys-Leu-Tyr-Gly-Lys-Cys-Arg-Arg-Tyr-4Hyp-Gly-Cys-Ser-Ser-Ala-Ser-Cys-Cys-Gln-Arg-$NH_2$ is synthesized by stepwise elongation from the carboxyl terminus, using the solid phase Merrifield peptide synthesis procedure. As generally set forth in Stewart, J. M. and Young, J., *Solid Phase Peptide Synthesis,* 2nd Ed., Pierce Chemical Co., Rockford, Ill., (1984), and in Rivier et al. U.S. Pat. No. 5,064,939, the disclosure of the latter of which is incorporated herein by reference.

A methylbenzyhydrylamine (MBHA) resin was used as the solid phase support, and after cleavage from the resin, the linear peptide was extracted using 200 milliliters of 50 percent acetic acid at a temperature below 0° C. Thereafter, the extracted peptide was washed once with methyl-tert-butyl ether (MTBE). The supernatant was discarded, and the pellet dissolved in 10 ml of 0.092 TFA and 60% $CH_3CN$ in $H_2O$. Peptide was then purified on a preparative column (Vydac $C_{18}$, 2.5×25 cm), eluted with a 6 to 30% $CH_3CN$ gradient and TFA buffer system at a flow rate of 20 ml/min.

Cysteine residues were oxidized using glutathione as described in Hopkins et al., *J. Biol. Chemistry,* 270, 22361–22367 (1995). The linear peptide was oxidized in a mixture of 1 mM/0.5 mM reduced/oxidized glutathione, pH 7.5, at room temperature. The equilibrium shift between these two glutathione forms fully oxidized the linear peptide into a mixture of isomers. The progress of the oxidation was monitored for 5–6 hours by analytical HPLC.

The major isomeric product (comprising about 65% of the isomer mixture) was purified by the HPLC. The native and synthetic peptides were compared by coelution on an analytical HPLC column, and the native and synthetic peptides appear to be identical to each other. The paralytic activity of native and synthetic peptides when injected intraperitoneally (ip) into goldfish was also comparable.

The paralytic effects of the peptide suggest that the toxin probably interferes with some step in neuromuscular transmission. The effect of the peptide on a freshly dissected electrocyte preparation from the weakly electric fish Eigenmannia was assessed. The electric organ of this teleost, as in electric rays such as Torpedo, is derived from muscle.

Synaptically mediated action potentials in Eigenmannia electrocytes evoked by electrical stimulation of the motor nerve in the spinal cord were monitored extracellularly. When the electrocyte preparation was exposed to the conotoxin peptide, the amplitude of the action potential was attenuated 100% by 10 $\mu$M and about 80% by 1 $\mu$M of the toxin. These results demonstrate the conotoxin peptide is a potent inhibitor of neuromuscular transmission in this teleost preparation. Such inhibition explains the paralytic activity observed in vivo when the peptide is injected into teleost fish.

Although these results suggest that this conotoxin is blocking neuromuscular transmission, they do not identify the molecular target of the toxin. The following experiments show that the peptide is directly inhibiting the function of the nicotinic acetylcholine receptor (nAChR).

The peptide was also tested on nAChRs expressed in Xenopus oocytes which had been injected with nAChR mRNA cloned from mouse skeletal muscle or from Torpedo electric organ. The conotoxin peptide inhibited the current normally elicited by acetylcholine, indicating that the toxin inhibits the nicotinic acetylcholine receptor. For the Torpedo receptor, the peptide has an $IC_{50}$ of 127 nM.

The peptide had no significant effect on a major neuronal nicotinic acetylcholine receptor subtype ($\alpha4\beta2$) expressed in the oocyte system. Thus, the peptide inhibits the skeletal muscle subtype of nicotinic acetylcholine receptors, and the results suggest that it may be relatively specific for this subtype.

Given the results indicating that the peptide functionally inhibits skeletal muscle nicotinic acetylcholine receptors, a binding competition experiment was carried out using a membrane preparation from Torpedo electric organ and $I^{125}$-α-bungarotoxin, the standard competitive ligand for the acetylcholine binding site. Binding assays were performed using a membrane fraction enriched in nAChR from *Torpedo californica* electroplax. The membrane preparation (0.38 pmol of α-bungarotoxin binding sites/$\mu$g of protein/0.1 ml of assay) was diluted with 0.02 M HEPES, pH 7.4; 5 mM EDTA; 0.5 mg/ml bovine serum albumin; and 0.5 mg/ml lysozyme. It was preincubated for 30 min. at room temperature with unlabeled synthetic peptide, followed by a 30 min. incubation with radioiodinated peptide (50,000 cpm/assay). Unbound radioligand was separated from receptor by centrifugation in a microcentrifuge for 3 min. at about 15000 g, and radioactivity in pellet and in supernatant was separately determined. The results demonstrate that the peptide does not compete for α-bungarotoxin binding. With the converse experiment using $I^{125}$-conotoxin peptide, the radiolabel is displaced by unlabeled conotoxin peptide (with an apparent $IC_{50}$ of 25 nM), but it is not displaced by α-bungarotoxin. Thus, although the conotoxin peptide functionally inhibits the acetylcholine receptor, it does so by a mechanism other than by competitive binding to the acetylcholine ligand site.

This peptide exhibits high affinity and specificity for the skeletal muscle nAChR and can be used to target this receptor or to assay for this receptor to the exclusion of neuronal nAChR.

EXAMPLE 2

A synthesis is carried out as generally set forth in Example 1 to produce a peptide having the following formula (SEQ ID NO:1):

H-His-4Hyp-4Hyp-Cys-Cys-Leu-Tyr-Gly-Lys-Cys-Arg-Arg-Tyr-4Hyp-Gly-Cys-Ser-Ser-Ala-Ser-Cys-Cys-Gln-Gly-$NH_2$.

The only difference between this peptide and that synthesized in Example 1 is the residue at the C-terminus, and accordingly the synthesis is again carried out on a MBHA resin. This time the first coupling reaction is carried out using Boc-Gly. The rest of the synthesis and the purification are carried out as in Example 1. The synthetic peptide exhibits biological activity essentially similar to that of the conotoxin synthesized in Example 1.

EXAMPLE 3

A synthesis is carried out as generally set forth in Example 1 to produce a peptide having the following formula (SEQ ID NO:1):

H-His-4Hyp-4Hyp-Cys-Cys-Leu-Tyr-Gly-Lys-Cys-Arg-Arg-Tyr-Pro-Gly-Cys-Ser-Ser-Ala-Ser-Cys-Cys-Gln-Arg-$NH_2$.

The only difference between this peptide and that synthesized in Example 1 is the 14-position residue is Pro instead of 4Hyp. The purification is carried out as in Example 1. The synthetic peptide exhibits biological activity generally similar to that of the conotoxin synthesized in Example 1.

EXAMPLE 4

A synthesis is carried out as generally set forth in Example 1 to produce a peptide having the following formula (SEQ ID NO:1):

H-His-4Hyp-Pro-Cys-Cys-Leu-Tyr-Gly-Lys-Cys-Arg-
Arg-Tyr-Pro-Gly-Cys-Ser-Ser-Ala-Ser-Cys-Cys-Gln-
Arg-NH$_2$.

The only difference between this peptide and that synthesized in Example 1 is the 3- and 14-position residues are Pro instead of 4Hpy. The purification is carried out as in Example 1. The synthetic peptide exhibits biological activity generally similar to that of the conotoxin synthesized in Example 1.

These synthetic peptides, for administration to humans, should have a purity of at least about 95 percent (herein referred to as substantially pure), and preferably have a purity of at least about 98 percent. Purity for purposes of this application refers to the weight of the intended peptide as compared to the weight of all peptide fragments present. These synthetic peptides, either in the free form or in the form of a nontoxic salt, are commonly combined with a pharmaceutically or veterinarily acceptable carrier to create a composition for administration to animals, including humans, or for use in in vitro assays. In vivo administration should be carried out by a physician and the required dosage will vary with the particular objective being pursued. In this respect, guidelines have been developed for the use of other conotoxins, such as conotoxin GI, as such are well known in this art and employed for the particular purpose of use.

Although the invention has been described with regard to certain preferred embodiments, it should be understood that various changes and modifications as would be obvious to one having the ordinary skill in the art may be made without departing from the scope of the invention which is set forth in appended claims. For example, substitution of one or more of the amino acid residues depicted in the amino acid sequence by residues known to be equivalent with those residues may be effected to produce equivalent peptides having similar biological activities. Moreover, it is known that additional substitutions in the amino acid sequence generally throughout the C-terminal portion of the peptide, i.e. within about ⅓ of the length of the conotoxin nearest its C-terminus, can be effected in order to produce conotoxins having phylogenetic specificity; thus, such substitutions in this region can be carried out to produce valuable equivalent structures. The C-terminus of each of the two illustrated peptides is amidated, and the inclusion of a substituted amide at the C-terminus of such peptides, as described hereinbefore, is considered to create an equivalent conotoxin.

Particular features of the invention are emphasized in the claims which follow.

What is claimed is:

1. A substantially pure conotoxin peptide having the formula (SEQ ID NO:1):
H-His-Xaa$_2$-Xaa$_3$-Cys-Cys-Leu-Tyr-Gly-Lys-Cys-Arg-Arg-Tyr-Xaa$_{14}$-Gly-Cys-Ser-Ser-Ala-Ser-Cys-Cys-Gln-Xaa$_{24}$-NH$_2$ wherein Xaa$_2$, Xaa$_3$ and Xaa$_{14}$ are independently Pro or 4Hyp and Xaa$_{24}$ is Arg or Gly.

2. The conotoxin peptide according to claim 1 wherein Xaa$_{24}$ is Arg.

3. The conotoxin peptide according to claim 2 wherein Xaa$_2$ is 4Hyp.

4. The conotoxin peptide according to claim 2 wherein Xaa$_3$ is 4Hyp.

5. The conotoxin peptide according to claim 2 wherein Xaa$_{14}$ is 4Hyp.

6. The conotoxin peptide according to claim 2 wherein Xaa$_2$, Xaa$_3$ and Xaa$_{14}$ are all 4Hyp.

7. The conotoxin peptide according to claim 1 wherein Xaa$_{24}$ is Gly.

8. The conotoxin peptide according to claim 7 wherein $Xaa_2$ is 4Hyp.

9. The conotoxin peptide according to claim 7 wherein $Xaa_3$ is 4Hyp.

10. The conotoxin peptide according to claim 7 wherein $Xaa_{14}$ is 4Hyp.

11. The conotoxin peptide according to claim 7 wherein $Xaa_2$, $Xaa_3$ and $Xaa_{14}$ are all 4Hyp.

* * * * *